United States Patent [19]

Hsu et al.

[11] Patent Number: 4,582,906

[45] Date of Patent: Apr. 15, 1986

[54] 4-PHENYL-1,2,3-THIADIAZOLES AS HERBICIDE EXTENDERS

[75] Inventors: Joanna K. Hsu, Sunnyvale; Arnold D. Gutman, Berkeley, both of Calif.

[73] Assignee: Stauffer Chemical Company, Westport, Conn.

[21] Appl. No.: 678,123

[22] Filed: Dec. 4, 1984

Related U.S. Application Data

[60] Division of Ser. No. 383,449, Jun. 1, 1982, Pat. No. 4,540,429, which is a continuation of Ser. No. 244,419, Mar. 16, 1981, abandoned.

[51] Int. Cl.$^4$ .......................................... C07D 285/06
[52] U.S. Cl. ..................................................... 548/127
[58] Field of Search ........................................ 548/127

[56] References Cited

U.S. PATENT DOCUMENTS 4,253,864 3/1981 Kloek .................................... 71/90

Primary Examiner—Robert Gerstl
Attorney, Agent, or Firm—Paul R. Martin; M. Henry Heines; Beth Kovitz

[57] ABSTRACT

Herbicidally active thiolcarbamates are employed in combination with certain 4-phenyl-1,2,3-thiadiazoles having the formula

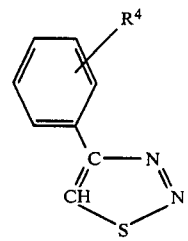

in which $R^4$ is selected from the group consisting of trifluoromethyl and

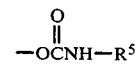

in which $R^5$ is selected from the group consisting of $C_1$–$C_3$ alkyl, phenyl, and phenyl substituted with one or more members selected from the group consisting of halogen and trifluoromethyl. In a typical application, the 4-phenyl-1,2,3-thiadiazole is included in sufficient quantity to lessen the rate of soil degradation of the thiolcarbamate. As a result, the herbicidal effectiveness of the thiolcarbamate is enhanced and prolonged, rendering a single application of the herbicide effective over a longer period of time.

5 Claims, No Drawings

4-PHENYL-1,2,3-THIADIAZOLES AS HERBICIDE EXTENDERS

This is a division of application Ser. No. 383,449, filed June 1, 1982, now U.S. Pat. No. 4,540,429, which in turn is a continuation of application Ser. No. 244,419, filed Mar. 16, 1981, now abandoned.

BACKGROUND OF THE INVENTION

This invention relates to herbicide extenders, herbicidal compositions, and herbicidal methods. In particular, this invention is addressed to the problem of herbicidal degradation occurring in certain soils.

Thiolcarbamates are well known in the agricultural art as herbicides useful for weed control in crops such as corn, potatoes, beans, beets, spinach, tobacco, tomatoes, alfalfa, and rice. Thiolcarbamates are primarily used in pre-emergence application, and are particularly effective when incorporated into the soil prior to the planting of the crop. The concentration of the thiolcarbamate in the soil is greatest immediately after application of the compound. How long thereafter the initial concentration is retained depends in large part on the particular soil used. The rate at which the thiolcarbamate concentration declines following its application varies from one type of soil to the next. This is evident both in the observable extent of weed control and in the detectable presence of undegraded thiolcarbamate remaining in the soil after considerable time has elapsed.

It is therefore an object of this invention to increase the soil persistence of thiolcarbamate herbicides and thus improve their herbicidal effectiveness.

BRIEF DESCRIPTION OF THE INVENTION

It has now been discovered that the soil persistence of certain herbicidally active thiolcarbamates is significantly extended by the further addition to the soil of certain extender compounds in the form of 4-phenyl-1,2,3-thiadiazoles, which have little or no herbicidal activity of their own and do not decrease the herbicidal activity of the thiolcarbamate. This improvement in the soil persistence of thiolcarbamates manifests itself in a variety of ways. It can be shown, for example, by soil analyses taken at regular intervals, that the rate of decrease of the thiolcarbamate content of the soil is substantially lessened. Improved soil persistence can also be shown by improvements in herbicidal efficacy, as evidenced by a higher degree of weed injury brought about when the extender compound increases the soil persistence of the thiolcarbamate, prolonging its effective life.

In particular, this invention relates to a novel herbicidal composition comprising (a) an herbicidally effective amount of a thiolcarbamate having the formula

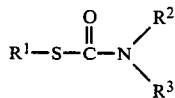

in which $R^1$, $R^2$, and $R^3$ are independently $C_2$–$C_4$ alkyl; and (b) an amount of a 4-phenyl-1,2,3-thiadiazole sufficient to extend the soil life of said thiolcarbamate, said 4-phenyl-1,2,3-thiadiazole having the formula

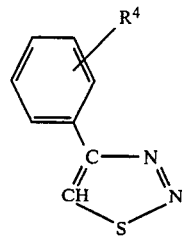

in which $R^4$ is selected from the group consisting of trifluoromethyl and

in which $R^5$ is selected from the group consisting of $C_1$–$C_3$ alkyl, phenyl, and phenyl substituted with one or more members selected from the group consisting of halogen and trifluoromethyl.

Within the scope of the present invention, certain embodiments are preferred, namely:

In the thiolcarbamate formula, $R^1$ is preferably ethyl, and $R^2$ and $R^3$ are each preferably propyl.

In the thiadiazole formula, $R^4$ is preferably selected from the group consisting of trifluoromethyl and

in which $R^5$ is selected from the group consisting of methyl, chlorophenyl, dichlorophenyl, trifluoromethylphenyl, and chlorotrifluoromethylphenyl. (The term "chlorotrifluoromethylphenyl" denotes a phenyl ring containing chlorine and trifluoromethyl as separate substituents.)

This invention further relates to a method of controlling undesirable vegetation comprising applying the above compositions to the locus where control is desired.

In addition, several of the above thiadiazoles are novel, namely those having the formula

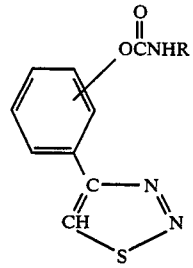

in which R is selected from the group consisting of $C_1$–$C_3$ alkyl, phenyl, and phenyl substituted with one or more members selected from the group consisting of halogen and trifluoromethyl.

Of these novel thiadiazoles, the preferred ones are those in which R is selected from the group consisting of methyl, chlorophenyl, dichlorophenyl, trifluoromethylphenyl, and chlorotrifluoromethylphenyl.

The term "alkyl" is used herein to include both straight-chain and branched-chain groups. All carbon atom ranges are inclusive of their upper and lower limits.

The term "herbicide," as used herein, means a compound or composition which controls or modifies the growth of plants. By the term "herbicidally effective amount" is meant any amount of such compound or composition which causes a modifying effect upon the growth of plants. By "plants" is meant germinant seeds, emerging seedlings, and established vegetation, including roots and above-ground portions. Such controlling or modifying effects include all deviations from natural development, such as killing, retardation, defoliation, desiccation, regulation, stunting, tillering, stimulation, leaf burn, dwarfing and the like.

The phrase "to extend the soil life of said thiolcarbamate" as used herein means to retard the rate at which molecules of thiolcarbamate are broken down into decomposition products when in contact with soil and/or to prolong the period of time following application in which herbicidal effects can be observed. This applies both to field sites where repeated applications of thiolcarbamates result in decreasing herbicidal effectiveness, and to field sites where a decline in herbicidal activity is detected over time regardless of the prior history of herbicidal applications. An extended soil life can be demonstrated by a slower rate of decline of weed-killing activity, or an increased half-life of thiolcarbamate concentration in the soil. Other techniques of determining soil life are readily apparent to one skilled in the art.

DETAILED DESCRIPTION OF THE INVENTION

Thiolcarbamates within the scope of the present invention can be prepared by the process described in U.S. Pat. No. 2,913,327 (Tilles et al., Nov. 17, 1959). Examples of such thiolcarbamates include S-ethyl N,N-di-n-propylthiolcarbamate, S-ethyl N,N-diisobutylthiolcarbamate, S-n-propyl N,N-di-n-propylthiolcarbamate, and S-n-propyl N-ethyl-N-n-butylthiolcarbamate.

Thiadiazoles within the scope of this invention can be prepared by processes described in Lemieux et al., U.S. Pat. No. 3,464,999 (Sept. 2, 1969). Generally, an appropriately substituted carbethoxyhydrazinoacetophenone is obtained by reacting the corresponding acetophenone with carbethoxyhydrazine in the presence of glacial acetic acid and a solvent such as methanol. The carbethoxyhydrazinoacetophenone is then reacted with thionyl chloride to produce the 4-phenyl-1,2,3-thiadiazole. The N-alkylcarbamoyloxyphenyl thiadiazoles can be produced from the hydroxyphenyl analog by reaction of the latter with an alkyl isocyanate.

The objects of the present invention are achieved by applying the extender compound to the soil at an agricultural field site in conjunction with the herbicide. The two compounds can be applied simultaneously in a single mixture or in separate formulations, or they can be applied in succession, with either one following the other. In successive application, it is preferable to add the compounds as close in time as possible.

The herbicide extending effect is operable over a wide range of ratios of the two compounds. It is most convenient, however, to apply the compounds at a ratio of about 1:1 to about 20:1 (herbicide:extender) on a weight basis, preferably about 1:1 to about 5:1, and most preferably about 1:1 to about 2:1.

The variety of crops on which the present composition is useful can be significantly broadened by the use of an antidote to protect the crop from injury and render the composition more selective against weeds.

For antidote descriptions and methods of use, reference is made to U.S. Pat. No. 3,959,304, issued to E. G. Teach on May 25, 1976; U.S. Pat. No. 3,989,503, issued to F. M. Pallos et al. on Nov. 2, 1976; U.S. Pat. No. 4,021,224, issued to F. M. Pallos et al. on May 3, 1977; U.S. Pat. No. 3,131,509, issued to O. L. Hoffman on May 5, 1964; and U.S. Pat. No. 3,564,768, issued to O. L. Hoffman on Feb. 3, 1971.

Examples of useful antidotes include acetamides such as N,N-diallyl-2,2-dichloroacetamide and N,N-diallyl-2-chloroacetamide, oxazolidines such as 2,2,5-trimethyl-N-dichloroacetyl oxazolidine and 2,2-spirocyclohexyl-N-dichloroacetyl oxazolidine, and 1,8-naphthalic anhydride. For maximum effect, the antidote is present in the composition in a non-phytotoxic, antidotally effective amount. By "non-phytotoxic" is meant an amount which causes at most minor injury to the crop. By "antidotally effective" is meant an amount which substantially decreases the extent of injury caused by the herbicide to the crop. The preferred weight ratio of herbicide to antidote is about 3:1 to about 20:1.

The first three examples which follow are offered to illustrate the preparation of the novel compounds of this invention. The activity of these compounds together with others falling within the broader scope of this invention is demonstrated in Examples 4 and 5.

EXAMPLE 1

4-(4'-N-Methylcarbamoyloxyphenyl)-1,2,3-thiadiazole

A reaction vessel was charged with 2.5 g (0.014 mole) of 4-(4'-hydroxyphenyl)-1,2,3-thiadiazole, 10 ml of methyl isocyanate, 5 ml of acetone, and 0.5 ml of triethylamine. The reactants were heated under reflux for one hour, then stripped in vacuo. The residue was poured into ice water and the solid product was collected by filtration and dried to yield 2.1 g of a solid with a melting point range of 156°–160° C. The molecular structure was confirmed by mass spectrometry as that of the title compound.

EXAMPLE 2

4-[2'-N-(3''-Trifluoromethylphenyl)carbamoyloxyphenyl]-1,2,3-thiadiazole

A reaction vessel was charged with 1.8 g (0.01 mole) of 4-(2'-hydroxyphenyl)-1,2,3-thiadiazole, 1.8 g (0.01 mole) of 3-trifluoromethylphenylisocyanate, 5 ml of methylene chloride, and three drops of triethylamine. The temperature of the mixture rose to 30° C. and the mixture was allowed to stand for one hour at ambient conditions. The mixture was then stripped in vacuo to yield 3.6 g of a glassy material (highly viscous liquid), whose molecular structure was confirmed by mass spectrometry as that of the title compound.

EXAMPLE 3

4-[2'-(3'',4''-Dichlorophenylcarbamoyloxy)phenyl]-1,2,3-thiadiazole

A reaction vessel was charged with 1.8 g (0.01 mole) of 4-(2'-hydroxyphenyl)-1,2,3-thiadiazole, 1.9 g (0.01 mole) of 3,4-dichlorophenylisocyanate, 25 ml of methylene chloride, and three drops of triethylamine. The temperature of the mixture rose to 35° C. After the exotherm subsided, the solvent was removed in vacuo to yield 3.5 g of a glassy material (highly viscous liquid), whose molecular structure was confirmed by mass spectrometry as that of the title compound.

EXAMPLE 4

This example shows, by soil analysis, the effectiveness of the thiadiazoles of the present invention in extending the soil life of thiolcarbamates. The thiolcarbamate used in this test was S-ethyl N,N-di-n-propylthiolcarbamate, commonly known as EPTC. The soil was a sandy loam soil obtained from Sunol, Calif., containing approximately (on a weight basis) 64% sand, 29% silt, and 7% clay, determined by mechanical means. The total organic content of the soil was approximately 4% by weight and the pH was 6.8, both determined by chemical analysis.

The test procedure involved an initial pre-treatment of the soil to simulate field conditions where the soil had been previously treated with EPTC, followed by a soil persistence test, as described below.

A. Soil Pre-Treatment

An emulsion was prepared by diluting an emulsifiable liquid concentrate containing 6 lb/gal (0.72 kg/l) of the thiolcarbamate in 100 ml of water, such that the concentration of thiolcarbamate in the resulting emulsion was 4000 mg/l. Five ml of this emulsion was then added to 10 lb (4.54 kg) of soil and the mixture was mixed in a rotary mixer for 10–20 seconds.

Round plastic containers, 9 inches (22.9 cm) in diameter by 9 inches (22.9 cm) deep, were then filled with the sandy loam soil, which was tamped and leveled with a row marker to impress three rows across the width of each container. Two rows were seeded with DeKalb XL-45A corn *Zea mays* (L.), and one row was seeded with barnyardgrass *Echinochloa crusgalli* (L.). Sufficient seeds were planted to produce several seedlings per row. The containers were then placed in a greenhouse maintained at 20° C. to 30° C. and watered daily by sprinkler.

Five weeks after treatment, the soil was allowed to dry out and the plant foliage was removed. The soil was then passed through a 0.25 inch (0.64 cm) screen, followed by a 2-millimeter (mm) screen, to remove plant roots and clods.

B. Soil Persistence Test

A 100-gram quantity (air-dry basis) of the pre-treated soil was placed in an 8-ounce (0.25 liter) wide-mouth glass bottle. The same emulsifiable concentrate described in Part A above was appropriately diluted in water such that a 5-ml portion added to the soil would produce a herbicide concentration of 6 ppm (weight) in the soil. This is equivalent to an application rate of 6 pounds per acre (6.7 kilograms) per hectare in a field where the herbicide is incorporated into the soil through a depth of about 2 inches (5.08 cm) soon after application. A selected extender compound in technical (nonformulated) form was then diluted in an acetone-water mixture such that a one-ml portion added to the soil would produce a concentration of 4 ppm by weight, equivalent to 4 pounds per acre (4.5 kilograms per hectare). On these bases, the herbicide and extender were added to the bottle containing the soil. The bottle was then sealed with a lid and shaken manually for approximately 15 minutes.

Following such treatment, the soil was moistened with 20 ml of deionized water. The bottle was then covered with a watch glass to maintain aerobic conditions and to prevent rapid soil drying, and placed in a controlled environmental chamber in darkness, where the temperature was maintained constant at 25° C.

Four days later, the bottle was removed from the environmental chamber and 25 ml of water and 100 ml of toluene were added. The bottle was then tightly sealed with a lid containing a cellophane liner, and vigorously shaken on a variable speed, reciprocating shaker (Eberbach Corp. Model 6000) set at approximately 200 excursions per minute for one hour. After shaking, the bottle contents were allowed to settle, and a 10 ml aliquot of toluene was transferred by pipette into a glass vial and sealed with a polyseal cap. The toluene extract was analyzed for herbicidal content by gas chromatography. The chromatogram data was then converted to equivalent soil concentrations in parts per million (ppm) by weight of the herbicide.

The results are shown in the table below, where the eight compounds were tested in three separately treated batches of soil. A control run without an extender compound was conducted for each soil batch, to show how the drop in herbicide concentration was affected by the extender compound. In each case, the quantity of herbicide remaining in the soil after four days was dramatically increased when the extender compound was added.

TABLE I

4-DAY SOIL PERSISTENCE DATA

Herbicide: S—Ethyl N,N—di-n-propylthiolcarbamate (EPTC) at 6 lb/A (6 ppm in soil)

Extender: As shown at 4 lb/A (4 ppm in soil)

| Extender Compound No. | Structural Formula | EPTC Residue After 4 Days (ppm) With Extender | Without Extender |
|---|---|---|---|
| Soil Batch A | | | |
| 1 | CH$_3$NHCO—⟨phenyl⟩—C=N, CH=S, N (thiadiazole) with C(=O) | 2.00 | 0.33 |
| 2 | ⟨phenyl with OC(=O)NHCH$_3$⟩—C=N, CH=S, N (thiadiazole) | 0.51 | 0.33 |
| Soil Batch B: | | | |
| 3 | ⟨phenyl with OC(=O)NH—(2,6-dichlorophenyl)⟩—C=N, CH=S, N (thiadiazole) | 1.99 | 0.03 |

TABLE I-continued

4-DAY SOIL PERSISTENCE DATA

Herbicide: S—Ethyl N,N—di-n-propylthiolcarbamate (EPTC) at 6 lb/A (6 ppm in soil)
Extender: As shown at 4 lb/A (4 ppm in soil)

| Extender Compound No. | Structural Formula | EPTC Residue After 4 Days (ppm) With Extender | Without Extender |
|---|---|---|---|
| 4 | [structure: OCNH-phenyl-Cl with thiadiazole] | 2.48 | 0.03 |
| 5 | [structure: OCNH-phenyl(CF3)-Cl with thiadiazole] | 1.58 | 0.03 |
| 6 | [structure: OCNH-phenyl-CF3 with thiadiazole] | 2.79 | 0.03 |
| 7 | [structure: OCNH-phenyl-Cl with thiadiazole] | 2.37 | 0.03 |
| Soil Batch C: | | | |
| 8 | [structure: CF3-phenyl with thiadiazole] | 1.17 | 0.04 |

EXAMPLE 5

Herbicidal Activity Improvement Tests

This example offers herbicidal activity test data to show the effectiveness of the extender compounds in improving the herbicidal activity of thiolcarbamates. The effect is observed by comparing the extent of weed control in test flats treated with a thiolcarbamate against that occurring in similar flats treated with both the thiolcarbamate and the extender.

As in Example 4, the thiolcarbamate used in this test was S-ethyl N,N-di-n-propylthiolcarbamate applied in the form of an emulsifiable liquid concentrate containing 6 lb/gal (0.72 kg/l) active ingredient. The extender compounds were used in technical form. These materials were added to a mixture of equal parts of acetone and water at such amounts that 5 cc of the resulting mixture when added to three pounds of soil yielded a quantity in the soil equivalent to the desired application rate expressed in pounds per acre. Thus, 5 cc of the mixture and three pounds of sandy loam soil from Keeton, Calif., containing approximately 10.8% sand, 24.8% silt, and 4.4% clay (by weight), with an organic content of 0.9% by weight and a pH of 7.2, were placed in a rotary mixer. Also added was 17-17-17 fertilizer ($N—P_2O_5—K_2O$ on a weight basis) at a quantity amounting to 50 ppm be weight with respect to the soil.

The treated soil was then placed in aluminum flats which were 2.5 inches deep, 3.5 inches wide, and 7.5 inches long (6.4 x 8.9 x 19.0 cm). The soil was tamped and leveled with a row marker to impress six rows across the width of the flat. The test weeds were as follows:

| Common Name | Scientific Name |
|---|---|
| green foxtail | *Setaria viridis* (L.) Beauv. |
| barnyardgrass | *Echinochloa crusgalli* (L.) Beauv. |
| sorghum | *Sorghum bicolor* (L.) Moench |
| wild oats | *Avena fatua* L. |
| shattercane | *Sorghum bicolor* (L.) Moench (variant of sorghum) |

DeKalb XI-45A corn of species *Zea mays* (L.) was also planted.

Sufficient seeds were planted to produce several seedlings per inch in each row. The flats were then placed in a greenhouse maintained at 70° to 85° F. and watered daily by sprinkler.

Three weeks after treatment, the degree of weed control and corn injury were estimated and recorded as percentage control compared to the growth of the same species in an untreated check flat of the same age. The rating scale ranges from 0 to 100%, where 0 equals no effect with plant growth equal to the untreated control, and 100 equals complete kill.

Table II lists the results of these tests. Control experiments are included for comparison. Substantial improvements in average percent weed control over the control experiments are evident and the herbicidal efficacy of the thiolcarbamate three weeks after application was much improved by the use of the extended.

TABLE II

HERBICIDAL ACTIVITY DATA

Herbicide: S—Ethyl N,N—di-n-propylthiolcarbamate (EPTC) at 3 lb/A
Extender: As shown
Evaluation Time: 3 weeks after treatment

| Extender Compound No. (see Table I) | Extender Application Rate | % Plant Injury Weed Average[1] | Corn |
|---|---|---|---|
| Control Data (no extender) | | 9.25[2] | 0 |
| Test Data | | | |
| 1 | 2.0 lb/A | 29 | 0 |
| 1 | 4.0 | 47 | 0 |
| 2 | 2.0 | 18 | 0 |
| 2 | 4.0 | 12 | 0 |
| 3 | 2.0 | 26 | 0 |
| 3 | 4.0 | 21 | 0 |
| 4 | 2.0 | 0 | 0 |
| 4 | 4.0 | 5 | 0 |
| 5 | 2.0 | 10 | 0 |
| 5 | 4.0 | 11 | 0 |
| 6 | 2.0 | 13 | 0 |
| 6 | 4.0 | 17 | 0 |
| 7 | 2.0 | 15 | 0 |
| 7 | 4.0 | 13 | 0 |
| 8 | 2.0 | 81 | 0 |

TABLE II-continued

HERBICIDAL ACTIVITY DATA

| Herbicide: | S—Ethyl N,N—di-n-propylthiolcarbamate (EPTC) at 3 lb/A |
|---|---|
| Extender: | As shown |
| Evaluation Time: | 3 weeks after treatment |

| Extender Compound No. (see Table I) | Extender Application Rate | % Plant Injury Weed Average[1] | Corn |
|---|---|---|---|
| 8 | 4.0 | 90 | 0 |

Notes:
[1] Average of injury to five weed species (green foxtail, barnyardgrass, sorghum, wild oats, shattercane).
[2] Figure for control data represents overall average of four replications.

METHODS OF APPLICATION

The herbicidal compositions of the present invention are useful in controlling the growth of undesirable vegetation by preemergence or post-emergence application to the locus where control is desired, including pre-plant and post-plant soil incorporation as well as surface application. The compositions are generally embodied in formulations suitable for convenient application, containing additional ingredients or diluent carriers to aid in the dispersal of the compositions. Examples of such ingredients or carriers are water, organic solvents, dusts, granules, surface active agents, water-oil emulsions, wetting agents, dispersing agents, and emulsifying agents. The formulated compositions generally take the form of dusts, emulsifiable concentrates, granules, or microcapsules.

A. Dusts

Dusts are dense powder compositions which combine the active compounds with a dense, free-flowing solid carrier. They are intended for application in dry form and are designed to settle rapidly to avoid being windborne to areas where their presence is not desired.

The carrier may be of mineral or vegetable origin, and is preferably an organic or inorganic powder of high bulk density, low surface area, and low liquid absorptivity. Suitable carriers include micaceous talcs, pyrophyllite, dense kaolin clays, tobacco dust, and ground calcium phosphate rock.

The performance of a dust is sometimes aided by the inclusion of a liquid or solid wetting agent, of ionic, anionic, or nonionic character. Preferred wetting agents include alkylbenzene and alkylnaphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, and ditertiary acetylenic glycols. Dispersants are also useful in the some dust compositions. Typical dispersants include methyl cellulose, polyvinyl alcohol, lignin sulfonates, polymeric alkylnaphthalene sulfonates, sodium naphthalene sulfonate, polymethylene bisnaphthalenesulfonate, and sodium-N-methyl-N-(long chain acid) taurates.

In addition, inert absorptive grinding aids are frequently included in dust compositions to aid in the manufacturing of the dust. Suitable grinding aids include attapulgite clay, diatomaceous silica, synthetic fine silica and synthetic calcium and magnesium silicates.

In typical dust compositions, carriers are usually present in concentrations of from about 30 to 90 weight percent of the total composition. The grinding aid usually constitutes about 5 to 50 weight percent, and the wetting agent up to about 1.0 weight percent. Dispersants, when present, constitute up to about 0.5 weight percent, and minor amounts of anticaking and antistatic agents may also be present. The particle size of the entire composition is usually about 30 to 50 microns.

B. Emulsifiable Concentrates

Emulsifiable concentrates are solutions in which the active materials and an emulsifying agent are dissolved in a nonwatermiscible solvent. Prior to use, the concentrate is diluted with water to form a suspended emulsion of solvent droplets.

Typical solvents for use in emulsifiable concentrates include weed oils, chlorinated hydrocarbons, and non-water-miscible ethers, esters, and ketones.

Typical emulsifying agents are anionic or nonionic surfactants, or mixtures of the two. Examples include long-chain mercaptan polyethoxy alcohols, alkylaryl polyethoxy alcohols, sorbitan fatty acid esters, polyoxyethylene ethers with sorbitan fatty acid esters, polyoxyethylene glycol esters with fatty or rosin acids, fatty alkylol amide condensates, calcium and amine salts of fatty alcohol sulfates, oil soluble petroleum sulfonates, or preferably mixtures of these emulsifying agents. Such emulsifying agents usually comprise about 1 to 10 weight percent of the total composition.

Typical emulsifiable concentrates contain about 15 to 50 weight percent active material, about 40 to 82 weight percent solvent, and about 1 to 10 weight percent emulsifier. Other additives such as spreading agents and stickers can also be included.

C. Granules

Granules are physically stable, particulate compositions in which the active ingredients adhere to or are distributed throughout a basic matrix of a coherent, inert carrier with macroscopic dimensions. A typical particle is about 1 to 2 millimeters in diameter. Surfactants are often present to aid in the leaching of the active ingredient from the granule to the surrounding medium.

The carrier is preferably of mineral origin, and generally falls within one of two types. The first are porous, absorptive, preformed granules, such as attapulgite or heat expanded vermiculite. A solution of the active agent is sprayed on the granule at concentrations of up to 25 weight percent of the total weight. The second are powdered materials to which the active ingredients are added prior to being formed into granules. These materials include kaolin clays, hydrated attapulgite, or bentonite clays in the form of sodium, calcium, or magnesium bentonites. Water-soluble salts may also be present to help the granules disintegrate in water. These ingredients are blended with the active components, then granulated or pelleted, followed by drying. In the resulting composition, the active component is distributed uniformly throughout the mass. Granules can be made with as much as 25 to 30 weight percent active component, but more frequently a concentration of about 10 weight percent is desired for optimum distribution. Granule compositions are most useful in a size range of 15–30 mesh.

The surfactant is generally a common wetting agent of anionic or nonionic character. The most suitable wetting agents depend upon the type of granule used. When preformed granules are sprayed with active material in liquid form, the most suitable wetting agents are nonionic, liquid wetters miscible with the solvent.

These are compounds generally known as emulsifiers, and comprise alkylaryl polyether alcohols, alkyl polyether alcohols, polyoxyethylene sorbitan fatty acid esters, polyethylene glycol esters with fatty or rosin acids, fatty alkylol amide condensates, oil solution petroleum or vegetable oil sulfonates, or mixtures of these. Such agents usually comprise up to about 5 weight percent of the total composition.

When the active ingredient is first mixed with a powdered carrier and subsequently granulated, liquid non-ionic wetters can still be used, but it is usually preferable to incorporate at the mixing stage a solid, powdered anionic wetting agent comprising up to about 2.0 weight percent of the total composition.

Typical granules comprise about 5 to 30 percent by weight active material, about 0 to 5 weight percent wetting agent, and about 65 to 95 weight percent carrier.

D. Microcapsules

Microcapsules are fully enclosed droplets or granules in which the active materials are enclosed in an inert porous membrane which allows the enclosed materials to escape to the surrounding medium at controlled rates.

Encapsulated droplets are typically about 1 to 50 microns in diameter. The enclosed liquid typically constitutes about 50 to 95% of the weight of the capsule, and may contain a small amount of solvent in addition to the active materials.

Encapsulated granules are characterized by porous membranes sealing the openings of the granule carrier pores, trapping the liquid containing the active components inside for controlled release. A typical granule size ranges from 1 millimeter to 1 centimeter in diameter. Granules formed by extrusion, agglomeration, or prilling are useful in the present invention as well as materials in their naturally occurring form. Examples of such carriers are vermiculite, sintered clay granules, kaolin, attapulgite clay, sawdust, and granular carbon.

Useful encapsulating materials include natural and synthetic rubbers, cellulosic materials, styrene-butadiene copolymers, polyacrylonitriles, polyacrylates, polyesters, polyamides, polyurethanes, and starch xanthates.

E. In General

Each of the above formulations can be prepared as a package containing both the herbicide and the extender together with the other ingredients of the formulation (diluents, emulsifiers, surfactants, etc.), or as a tank mix in which the components are formulated separately and combined at the grower site. The two formulations in the tank mix can be of either the same type or two different types—e.g., the herbicide in microcapsule form and the extender as an emulsifiable concentrate. As a further alternative, the herbicide and extender can be applied sequentially. This is less preferred, however, since simultaneous application generally produces better results.

In general, any conventional method of application can be used. The locus of application can be soil, seeds, seedlings, or the actual plants, as well as flooded fields. Soil application is preferred. Dusts and liquid compositions can be applied by the use of powder dusters, boom and hand sprayers, and spray dusters. The compositions can also be applied from airplanes as dusts and sprays because they are effective in very low dosages. In order to modify or control the growth of germinating seeds or emerging seedlings, as a typical example, the dust and liquid compositions are applied to the soil according to conventional methods and are distributed to a depth of at least one-half inch below the soil surface. The compositions can either be mixed with the soil particles by discing, dragging, or mixing operations, or sprayed or sprinkled over the surface of the soil. The compositions can also be added to irrigation water so that they will accompany the water as it penetrates the soil.

The amount of active ingredient required for herbicidal effectiveness depends upon the nature of the seeds or plants to be controlled and the prevailing conditions. Usually, herbicidal effects are obtained with an application rate of about 0.01 to about 50 pounds per acre, preferably about 0.1 to about 25. It will be readily apparent to one skilled in the art that compositions exhibiting lower herbicidal activity will require a higher dosage than more active compounds for the same degree of control.

What is claimed is:

1. A compound having the formula

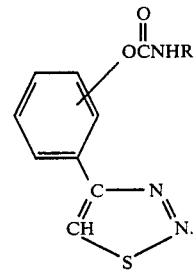

in which R is selected from the group consisting of $C_1$–$C_3$ alkyl, phenyl, and phenyl substituted with one or more members selected from the group consisting of halogen and trifluoromethyl.

2. A compound according to claim 1 in which R is selected from the group consisting of methyl, chlorophenyl, dichlorophenyl, trifluoromethylphenyl, and chlorotrifluoromethylphenyl.

3. A compound according to claim 1 having the formula

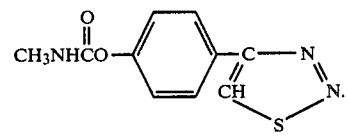

4. A compound according to claim 1 having the formula

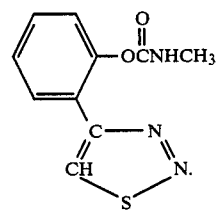

5. A compound according to claim 1 having the formula

13
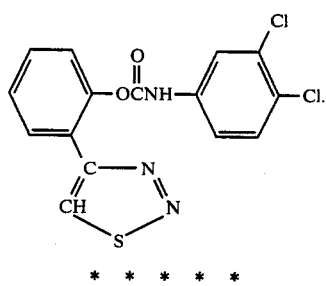
* * * * *
14
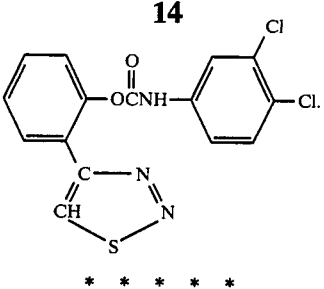
* * * * *